(12) United States Patent
Lumme et al.

(10) Patent No.: US 10,300,201 B2
(45) Date of Patent: May 28, 2019

(54) PLUNGER SUB-ASSEMBLIES AND AUTO-INJECTORS HAVING LOW RETRACTION ACTIVATION FORCE

(71) Applicant: UNL Holdings LLC, New York, NY (US)

(72) Inventors: Katlin M. Lumme, Mableton, GA (US); Philip A. Weaver, Denver, PA (US)

(73) Assignee: UNL Holdings LLC, New York, NY (US)

( * ) Notice: Subject to any disclaimer, the term of this patent is extended or adjusted under 35 U.S.C. 154(b) by 604 days.

(21) Appl. No.: 14/376,758

(22) PCT Filed: Feb. 6, 2013

(86) PCT No.: PCT/US2013/024819
§ 371 (c)(1),
(2) Date: Aug. 5, 2014

(87) PCT Pub. No.: WO2013/119591
PCT Pub. Date: Aug. 15, 2013

(65) Prior Publication Data
US 2014/0364812 A1 Dec. 11, 2014

Related U.S. Application Data

(60) Provisional application No. 61/595,539, filed on Feb. 6, 2012.

(51) Int. Cl.
*A61M 5/20* (2006.01)
*A61M 5/46* (2006.01)
(Continued)

(52) U.S. Cl.
CPC ...... *A61M 5/2033* (2013.01); *A61M 5/31511* (2013.01); *A61M 5/322* (2013.01);
(Continued)

(58) Field of Classification Search
CPC ............ A61M 5/2033; A61M 5/31511; A61M 5/322; A61M 5/46; A61M 2005/206;
(Continued)

(56) References Cited

U.S. PATENT DOCUMENTS 3,395,704 A    8/1968   Frey et al.
5,211,628 A *   5/1993   Marshall ............. A61M 5/3234
                                                                                128/919
(Continued)

FOREIGN PATENT DOCUMENTS

AU      2003275893 B2    6/2004
CN       100553700 C    10/2009
(Continued)

OTHER PUBLICATIONS

European Patent Office, International Search Report in International Application No. PCT/US2012/052129, 5 pages (dated Dec. 11, 2012).
(Continued)

*Primary Examiner* — Nathan R Price
*Assistant Examiner* — Anh Bui
(74) *Attorney, Agent, or Firm* — Hamilton, Brook, Smith & Reynolds, P.C.

(57) ABSTRACT

A low retraction activation force plunger sub-assembly for an automatic injector includes: a plunger outer having one or more engagement prongs, a plunger inner having a shoulder, and a plunger biasing member retained in a first energized state between said plunger outer and plunger inner when the engagement prongs of the plunger outer are releasably engaged with the shoulder of the plunger inner. An automatic injector includes a housing, an activation mechanism, an actuation mechanism, and a syringe cartridge having the plunger sub-assembly and a needle assembly, wherein the actuation mechanism includes comprises an actuation bias-
(Continued)

ing member residing in an initial energized state substantially within an upper portion of an actuation pill. A method of assembling the automatic injector includes the steps of: assembling the plunger sub-assembly and inserting the plunger sub-assembly into the housing such that a proximal end of the plunger sub-assembly contacts the actuation pill.

22 Claims, 14 Drawing Sheets

(51) Int. Cl.
*A61M 5/32* (2006.01)
*A61M 5/315* (2006.01)

(52) U.S. Cl.
CPC ........ *A61M 5/3232* (2013.01); *A61M 5/3234* (2013.01); *A61M 5/46* (2013.01); *A61M 2005/206* (2013.01); *A61M 2005/208* (2013.01); *A61M 2005/2073* (2013.01); *A61M 2005/3235* (2013.01); *A61M 2005/3236* (2013.01); *A61M 2005/3238* (2013.01); *A61M 2005/3239* (2013.01); *A61M 2005/3241* (2013.01); *A61M 2207/00* (2013.01); *Y10T 29/49826* (2015.01)

(58) Field of Classification Search
CPC .... A61M 2005/208; A61M 2005/2073; A61M 5/3232; A61M 5/3234; A61M 2005/3235; A61M 2005/3236; A61M 2005/3238; A61M 2005/3239; A61M 2005/3241
See application file for complete search history.

(56) References Cited

U.S. PATENT DOCUMENTS

| | | | |
|---|---|---|---|
| 5,425,715 | A | 6/1995 | Dalling et al. |
| 6,083,199 | A | 7/2000 | Thorley et al. |
| 6,090,070 | A | 7/2000 | Hager et al. |
| 6,387,078 | B1 | 5/2002 | Gillespie, III |
| 6,607,508 | B2 | 8/2003 | Knauer |
| 7,381,201 | B2 | 6/2008 | Gilbert et al. |
| 7,500,967 | B2 | 3/2009 | Thorley et al. |
| 7,736,353 | B2 | 6/2010 | Reynolds |
| 7,744,582 | B2 | 6/2010 | Sadowski et al. |
| 7,935,087 | B2 | 5/2011 | Judd et al. |
| 8,002,745 | B2 | 8/2011 | Kaal et al. |
| 8,021,333 | B2 | 9/2011 | Kaal et al. |
| 8,052,654 | B2 | 11/2011 | Kaal et al. |
| 8,114,050 | B2 | 2/2012 | Kaal et al. |
| 8,167,937 | B2 | 5/2012 | Cerruti et al. |
| 8,366,669 | B2 | 2/2013 | Donald et al. |
| 8,702,653 | B2 | 4/2014 | Samandi et al. |
| 8,808,244 | B2 | 8/2014 | Adlon et al. |
| 2003/0004468 | A1* | 1/2003 | Righi ................... A61M 5/3234 604/243 |
| 2005/0080377 | A1 | 4/2005 | Sadowski et al. |
| 2005/0277886 | A1 | 12/2005 | Hommann et al. |
| 2009/0254048 | A1 | 10/2009 | Hetherington |
| 2011/0015572 | A1 | 1/2011 | Thorley et al. |
| 2011/0092954 | A1 | 4/2011 | Jennings |
| 2011/0213314 | A1* | 9/2011 | Guillermo ........... A61M 5/2033 604/198 |
| 2012/0056019 | A1 | 3/2012 | Renz et al. |
| 2013/0060233 | A1* | 3/2013 | O'Connor et al. ... A61M 5/158 604/506 |

FOREIGN PATENT DOCUMENTS

| | | |
|---|---|---|
| CN | 101730558 A | 6/2010 |
| DE | 20 2009 003009 U1 | 6/2009 |
| EP | 2331171 | 6/2011 |
| FR | 1538565 A | 9/1968 |
| JP | 2007-504867 A | 3/2007 |
| JP | 2008-543500 A | 12/2008 |
| WO | WO 1994/21316 A1 | 9/1994 |
| WO | WO 95/04562 A1 | 2/1995 |
| WO | WO 03/008023 A1 | 1/2003 |
| WO | WO 2004/000395 A1 | 12/2003 |
| WO | WO 2004/047890 A1 | 6/2004 |
| WO | WO 2004/047891 A1 | 6/2004 |
| WO | WO 2005/018721 A1 | 3/2005 |
| WO | WO 2006/108243 A2 | 10/2006 |
| WO | WO 2006/119570 A1 | 11/2006 |
| WO | WO 2007/002052 A2 | 1/2007 |
| WO | WO 2007/036676 A1 | 6/2007 |
| WO | WO 2009/003234 A1 | 1/2009 |
| WO | WO 2009/007229 A1 | 1/2009 |
| WO | WO 2009/063030 A1 | 5/2009 |
| WO | WO 2009/153540 A1 | 12/2009 |
| WO | WO 2009/153543 A1 | 12/2009 |
| WO | WO 2010/049239 A1 | 5/2010 |
| WO | WO 2011/057335 A1 | 5/2011 |
| WO | WO 2011/075760 A1 | 6/2011 |
| WO | WO 2013/028906 A1 | 6/2011 |
| WO | WO 2011/089417 A1 | 7/2011 |
| WO | WO 2011/109205 A1 | 9/2011 |
| WO | WO 2011/137488 A1 | 11/2011 |
| WO | WO 2011/141907 A1 | 11/2011 |
| WO | WO 2012/098371 A1 | 7/2012 |

OTHER PUBLICATIONS

European Patent Office, Written Opinion of the International Searching Authority in International Application No. PCT/US2012/052129, 6 pages (dated Dec. 11, 2012).

European Patent Office, International Search Report in International Application No. PCT/US2013/024819, 5 pages, dated Apr. 16, 2013.

European Patent Office, Written Opinion of the International Searching Authority in Application No. PCT/US2013/024819, 8 pages, dated Apr. 16, 2013.

European Patent Office, International Search Report and Written Opinion in International Patent Application No. PCT/US2013/049314, dated Oct. 15, 2013, 11 pages.

European Patent Office, International Preliminary Report on Patentability in International Application No. PCT/US2013/024819, 8 pgs (dated Aug. 21, 2014).

* cited by examiner

PLUNGER SUB-ASSEMBLIES AND AUTO-INJECTORS HAVING LOW RETRACTION ACTIVATION FORCE

CROSS-REFERENCE TO RELATED APPLICATIONS

This application claims priority to U.S. Provisional Application No. 61/595,539, filed on Feb. 6, 2012, which is included by reference herein in its entirety for all purposes.

FIELD

THIS INVENTION relates to automatic injectors for retractable syringes. More particularly, this invention relates to plunger sub-assemblies for automatic injectors and automatic injectors for retractable syringes having low retraction activation force, the methods of operating such devices, and the methods of assembling such devices.

BACKGROUND

Manually activated syringes are commercially available from a variety of manufacturers, including the owner and assignee of the present invention, and are used in the administration of drug solutions, drug suspensions, vaccines, medicinal therapies, and any other liquid medicament by parenteral injection. Such syringes are commonly utilized by medical practitioners to administer injections to patients but are difficult to use by self-administering patients.

An auto-injector is an automatic injection device designed to facilitate delivery of a dose of medicament to a patient through a hypodermic needle, the injection usually being administered by the patient themselves. An auto-injector works, for example, by delivering an injection automatically upon activation by the patient. This is in contrast to a conventional manually activated syringe where the patient themselves needs to directly depress a plunger into a barrel containing medicament in order to effect the injection. Auto-injectors have proven particularly useful in allowing the medically untrained user to administer a parenteral injection, and can provide both psychological and physical advantages to patients. Patients needing to inject medication for chronic disease management have used auto-injectors since the first reusable auto injector was introduced in the 1990s. An auto injector provides protection for the primary container, generally a pre-filled syringe, and offers an easy-to-use solution for automatic injection of medication. As used herein, the terms "automatic injector" and "auto-injector" are meant to refer to the same devices.

In addition to automatic needle insertion and dose delivery, some auto-injectors also incorporate safety mechanisms to automatically protect the patient from the needle after use. The automatic injectors of the prior art are usually provided with needle shields which extend over the needle when actuated. However, such safety mechanisms may fail to actuate and/or can be easily reversed, thereby leaving the patient exposed to the needle and susceptible to injury. Additionally, known automatic injectors generally link visual, tactile or audible indicators to the end of plunger stroke or actuation of some safety mechanism, instead of to the end of drug dose. Accordingly, the self-administering patient is not provided with an indication that the drug has been fully delivered and may remove the needle or actuate the safety mechanisms prematurely.

SUMMARY

The present invention provides plunger sub-assemblies for automatic injectors and automatic injectors for retractable syringes having low retraction activation force, the methods of operating such devices, and the methods of assembling such devices. The automatic injectors of the present invention provide integrated safety features which automatically retract the needle or cannula into the device to, for example, prevent injuries related to accidental needlestick. Additionally, the embodiments of the present invention provide true end of dose indication to users, informing the user that the drug delivery has completed and that the device is safe for removal and disposal. Furthermore, the embodiments of the present invention provide plunger sub-assemblies which reduce forces required to activate retraction of the needle or cannula, thereby providing significant manufacturing, assembly, and operational benefits. Accordingly, the novel devices of the present invention alleviate one or more of the problems associated with prior art devices, such as those referred to above.

In a first embodiment, the present invention provides a low retraction activation force plunger sub-assembly for an automatic injector. The plunger sub-assembly includes a plunger outer having one or more engagement prongs, a plunger inner having a shoulder, and a plunger biasing member. In at least one embodiment, the plunger outer has two engagement prongs for releasable engagement with the shoulder of the plunger inner. The plunger biasing member, which may be a spring such as a compression spring, is retained in a first energized state between the plunger outer and plunger inner when the engagement prongs of the plunger outer are releasably engaged with the shoulder of the plunger inner. In at least one embodiment, the plunger biasing member is a compression spring. The plunger spring may be held in the first energized state between a ledge of the plunger inner and a base of the plunger outer. The one or more engagement prongs are capable of flexing substantially radially to release from engagement with the shoulder of the plunger inner to permit the plunger spring to expand from the first energized state to a second expanded state. In at least one embodiment, the plunger inner has a seal-engaging member to engage a complementary engagement recess of a plunger seal. The seal-engaging member may be, for example, a screw-threaded aspect that is capable of screwing into the engagement recess of the plunger seal.

In another embodiment, the present invention provides an automatic injector having a low retraction activation force sub-assembly. The automatic injector includes a housing, an activation mechanism, an actuation mechanism, and a syringe cartridge having a plunger sub-assembly and a needle assembly. The actuation mechanism includes an actuation biasing member residing in an initial energized state substantially within an upper portion of an actuation pill. In at least one embodiment, the plunger sub-assembly includes a plunger outer having one or more engagement prongs, a plunger inner having a shoulder, and a plunger biasing member retained in a first energized state between said plunger outer and plunger inner when the engagement prongs of the plunger outer are releasably engaged with the shoulder of the plunger inner. The actuation biasing member and the plunger biasing member may each be a compression spring in at least one embodiment of the present invention.

The actuation pill has one or more locking hooks at a proximal end of the first actuation pill which initially engage a locking plateau at an interior proximal end of the housing. The activation mechanism is capable of engaging or contacting the one or more locking hooks of the actuation pill to disengage the locking hooks from the locking plateau of the housing. The housing may further include one or more recesses on the inner surface of the housing wherein, when the one or more engagement prongs interface with the recesses, the substantially radial flexion of the engagement prongs into the recesses permits the engagement prongs to disengage from the shoulder of the plunger inner. This disengagement permits the plunger biasing member to expand from the first energized state to a second expanded state for retraction of the needle assembly. Accordingly, little or no additional force is needed to disengage the plunger outer from the plunger inner beyond the force utilized to axially translate the plunger sub-assembly to the portion of the housing where the engagement prongs may radially flex into the recesses.

Accordingly, by user action on the activation mechanism, the activation mechanism engages or contacts the one or more locking hooks of the actuation pill to disengage the locking hooks from the locking plateau of the housing. This action permits the actuation spring to expand, thereby translating the actuation mechanism within the housing in the distal direction substantially along the axis of the automatic injector. As the engagement prongs of the plunger sub-assembly reach recesses within the inner surface of the housing, the one or more engagement prongs of the plunger outer are permitted to flex substantially radially to disengage from the corresponding shoulder of the plunger inner. This action permits the plunger spring to expand, thereby translating the plunger inner in the proximal direction substantially along the axis of the automatic injector for retraction of the needle assembly. If the syringe cartridge contains a drug treatment, such as in the case of a pre-filled syringe, the function of the actuation mechanism may be utilized to insert a needle and deliver the drug treatment into a patient. Optionally, when a retractable syringe is utilized as a syringe cartridge, the actuation mechanism may further be utilized to activate a retraction mechanism.

In a preferred embodiment of the present invention, the syringe cartridge of the automatic injector is a retractable syringe. Such syringes may further contain safety features which retract the needle after use, providing desirable needle-stick prevention, and prevent re-use of the syringe. Suitably, the plunger sub-assembly is slidably moveable within the barrel of the syringe to thereby facilitate delivery of the drug treatment to a user, patient or other recipient. The retractable syringe may include a retractable needle assembly. Preferably, the plunger sub-assembly is capable of engaging or contacting the needle assembly, or a portion thereof, to cause retraction of the cannula or needle. Suitably, retraction of the needle is facilitated by a biasing member such as a spring, elastic or other member capable of storing and releasing energy to facilitate needle retraction. It will be appreciated that the retractable syringe may comprise any needle retraction mechanism that is operable with the automatic injector disclosed herein. By way of example, the needle retraction mechanism may be as described in International Publication WO2006/119570, International Publication WO2006/108243, International Publication WO2009/003234 and International Publication WO2011/075760, and/or U.S. patent application Ser. No. 13/693,915, although without limitation thereto.

According to one embodiment, the retractable syringe comprises: a needle assembly comprising the retractable needle, wherein the retractable needle comprises a cannula and a needle seal engageable by the plunger seal mounted to the plunger inner. Preferably, the needle assembly is configured such that the needle seal retains the retractable needle and the cannula of the retractable needle passes through the needle seal to permit delivery of the mixed substances or mixture to a user, patient, or other recipient. In one embodiment, the needle assembly is similar to that disclosed in International Publication WO2011/075760 which includes a needle body that is capable of being captured by the plunger seal, such as within a recess within the plunger seal, for retraction into the barrel of the syringe cartridge and/or the housing of the automatic injector. In an alternative embodiment, the needle assembly may be similar to that disclosed in U.S. patent application Ser. No. 13/693, 915 which does not require a needle body and which activates retraction of the cannula through contact between the plunger seal and needle seal.

In at least one embodiment of the present invention, the automatic injector further includes a sleeve having one or more protrusions that are initially held by a cap in an engaged position within corresponding notches on the interior surface of housing. Upon removal of the cap, protrusions are permitted to flex radially inwards to disengage from the notches. The sleeve is configured to permit axial translation in a distal direction until a bridge portion of sleeve contacts a corresponding depth limiter on the interior surface of the housing. The automatic injector further includes one or more windows within the housing to view the internal components and function of the automatic injector. The windows may be transparent, opaque, or translucent, for example. The automatic injector may also include a tactile biasing member, such as a compression spring, between the activation mechanism and the proximal end of the housing.

In yet another embodiment, the present invention provides a method of assembling the automatic injector. The method of assembly includes: (i) inserting an actuation biasing member into a housing and compressing the actuation biasing member between the housing and the actuation pill by detachably engaging one or more locking hooks of the actuation pill with a locking plateau of the housing; (ii) assembling a plunger sub-assembly including a plunger outer having one or more engagement prongs, a plunger inner having a shoulder, and a plunger biasing member retained in a first energized state between said plunger outer and plunger inner when the engagement prongs of the plunger outer are releasably engaged with the shoulder of the plunger inner; and (iii) inserting the plunger sub-assembly into the housing such that a proximal end of the plunger sub-assembly contacts the actuation pill. The actuation biasing member is initially maintained in an energized state substantially within an upper portion of the actuation pill. In another embodiment, the method further includes the step of: attaching an activation mechanism to the housing wherein the activation mechanism is configured to contact the one or more locking hooks of the first actuation pill upon activation. The engagement prongs of the plunger outer are maintained in a releasably engaged configuration with the shoulder of the plunger inner by a first inner diameter of the housing. The method may further include the steps of (iv) filling a drug chamber of a syringe cartridge with a drug fluid, and (v) inserting the distal end of the plunger sub-assembly into the proximal end of the syringe cartridge. Steps (iv) and (v) may occur before or after step (iii).

Throughout this specification, unless otherwise indicated, "comprise," "comprises," and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to the following drawings wherein.

DETAILED DESCRIPTION

Figure 1A:
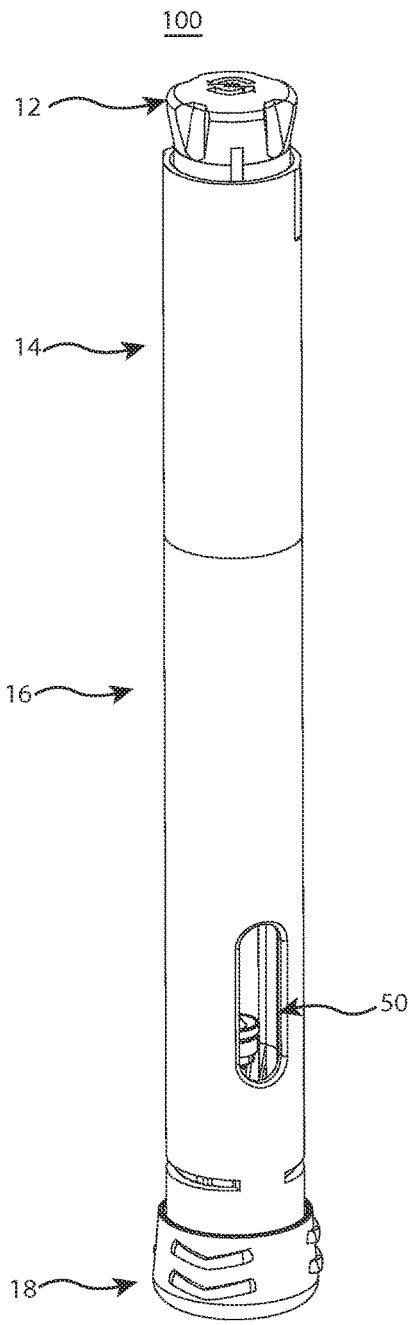
FIG. 1A shows an isometric view of an automatic injector, according to one embodiment of the present invention.

The novel devices of the present invention provide integrated safety features which automatically retract a needle or cannula into the device and provide true end of dose indication to users. Additionally, the embodiments of the present invention reduce the forces necessary to activate the needle retraction features of the device, thereby providing operational and manufacturing advantages. Such devices are safe and easy to use, and are aesthetically and ergonomically appealing for self-administering patients. The devices described herein incorporate features which make activation, operation, and lock-out of the device simple for even untrained users. The embodiments of the present invention provide these desirable features without any of the problems associated with known prior art devices.

As used herein to describe the actuation mechanisms, plunger sub-assemblies, automatic injectors, syringe cartridges, or any of the relative positions of the components of the present invention, the terms "axial" or "axially" refer generally to a longitudinal axis "A" around which the components of the automatic injectors are preferably positioned, although not necessarily symmetrically therearound. The term "radial" refers generally to a direction normal to axis A. The terms "proximal," "rear," "rearward," "back," or "backward" refer generally to an axial direction in the direction "P" of the activation mechanism. The teams "distal," "front," "frontward," "depressed," or "forward" refer generally to an axial direction in the direction "D" of the needle. As used herein, the term "glass" should be understood to include other similarly non-reactive materials suitable for use in a pharmaceutical grade application that would normally require glass. The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" does not include either glass or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration. "Fluid" refers primarily to liquids, but can also include suspensions of solids dispersed in liquids, and gasses dissolved in or otherwise present together within liquids inside the fluid-containing portions of syringes. The term "spring" is used herein with reference to one or more "biasing members," and any type of spring or other biasing member may be utilized within the inventions herein.

Figure 1B:
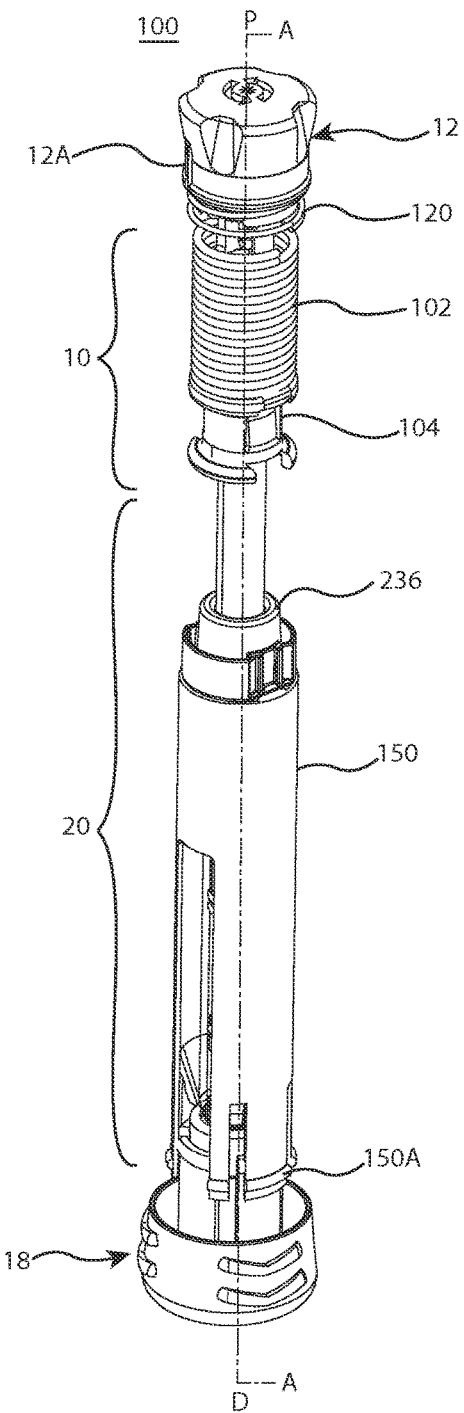
FIG. 1B shows an isometric view of the interior components of the automatic injector shown in FIG. 1A.
Figure 2:
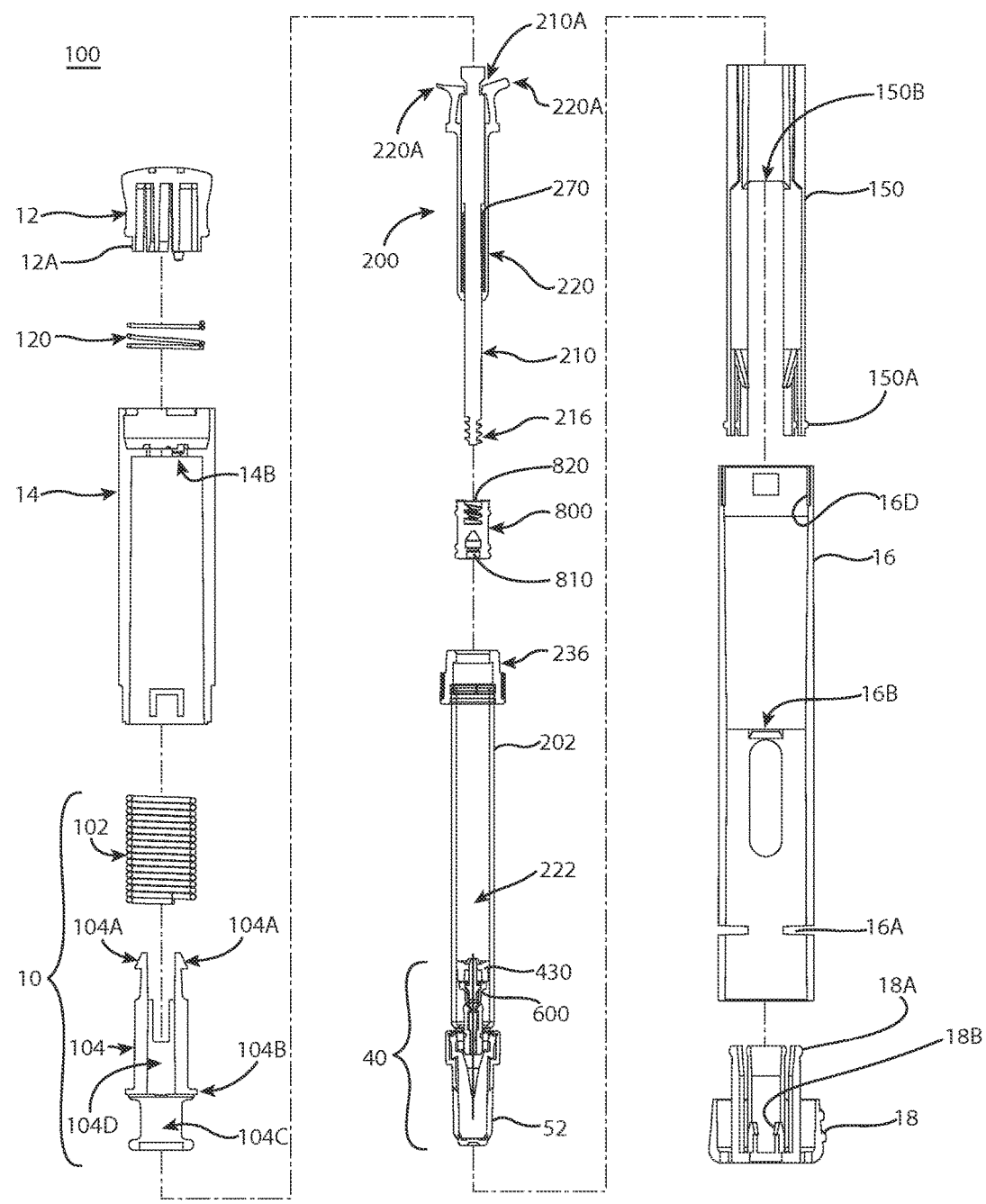
FIG. 2 shows an exploded view of an automatic injector, according to one embodiment of the present invention.

FIG. 1A and FIG. 1B show an embodiment of automatic injector 100 which includes upper housing 14 and lower housing 16. Upper housing 14 and lower housing 16 may be made of any of a number of materials including plastics and glass, but are preferably made of plastic. Upper housing 14 and lower housing 16 may be one unified component consisting of two portions or, as shown in FIGS. 1A and 1B, two separate components. When upper housing 14 and lower housing 16 are two separate components they may be fixedly connected, for example by a glue or adhesive, or removably attached, for example by a screw-fit connection. Automatic injector 100 may also include activation mechanism 12 and cap 18. FIG. 1B shows the interior components of automatic injector 100, i.e., with the upper housing 14 and lower housing 16 hidden from view. As shown in FIG. 1B, automatic injector 100 includes activation mechanism 12, actuation mechanism 10, and syringe cartridge 20. The syringe cartridge 20 includes a plunger sub-assembly 200 and a needle assembly 40, both of which are shown in FIG. 2. FIG. 2 shows how the novel plunger sub-assembly 200, actuation mechanism 10, and other components are assembled to produce an automatic injector 100, according to at least one embodiment of the present invention. The automatic injector may also include a sleeve 150 to assist in the positioning of the syringe cartridge 20 and needle assembly throughout the operation of the device, as is described further herein with reference to FIGS. 5-8. Cap 18 may be removably attached to automatic injector 100 at the distal end D of the device and removed at time of use by the user. FIG. 1B shows the components of actuation mechanism 10, the syringe cartridge 20 having a plunger sub-assembly, and automatic injector 100, according to at least one embodiment of the present invention, in a locked configuration.

In at least one embodiment, the activation mechanism 12 is a button which may, for example, be rotated to unlock the device and depressed to activate the device, as is detailed further herein. The activation mechanism is shown at proximal end P of automatic injector 100. A tactile biasing member 120 may be utilized, for example, between the activation mechanism 12 and the proximal end of the upper housing 14 to maintain the activation mechanism in a locked position until manipulation by the user and/or to provide the user with a tactile feedback when the activation mechanism is depressed. Typically, syringe cartridge 20 includes a barrel having a drug chamber. A liquid substance or drug dose is held in the drug chamber for delivery through a needle assembly to a patient. Upon depression, i.e., axial motion in the distal direction, activation mechanism 12 permits actuation mechanism 10 to actuate the needle insertion and drug dose delivery stages of operation. The actuation mechanism 10 also translates a plunger sub-assembly in the distal direction to facilitate or initiate the retraction activation stage of operation. Retraction activation by the actuation mechanism 10 enables retraction of the needle assembly into the barrel of the syringe cartridge and automatic injector 100, as is detailed further herein.

The automatic injectors of the present invention utilize one or more biasing members, such as compression springs, to provide the force necessary to insert the needle into the user, push fluid from the drug chamber of the syringe cartridge out through the needle assembly for drug delivery, and activate a needle retraction safety mechanism. However, it is important to minimize the force necessary to be provided by such biasing members for various manufacturing and operational benefits. For example, a lower force biasing member, which may be more cost-effective than higher force biasing members, may be utilized if reduced forces are needed to perform all of the stages of device operation. Similarly, reducing necessary forces may enable the devices to be stored and transported more readily since the energy stored within the device prior to activation is reduced. Accordingly, the embodiments of the present invention utilize novel plunger sub-assemblies which require lower forces to initiate activation of the retraction mechanism. Because the plunger sub-assemblies and the integrated retraction features are driven, or caused to activate, by the actuation mechanism, the actuation mechanisms and the automatic injectors of the present invention may be configured to utilize lower force biasing members. Similarly, because the total force necessary to insert the needle into the user, deliver the drug fluid, and activate the needle retraction mechanism is reduced, a simplified actuation mechanism, such as an actuation mechanism having only one actuation pill and actuation spring, may be utilized to efficiently deliver all of the force necessary for the operation of the device. This advantage of the novel plunger sub-assemblies of the present invention, and their integration into the actuation mechanism, provides substantial benefits to the manufacturability, stability, and operability of the novel automatic injectors described herein.

Figures 3A, 3B:
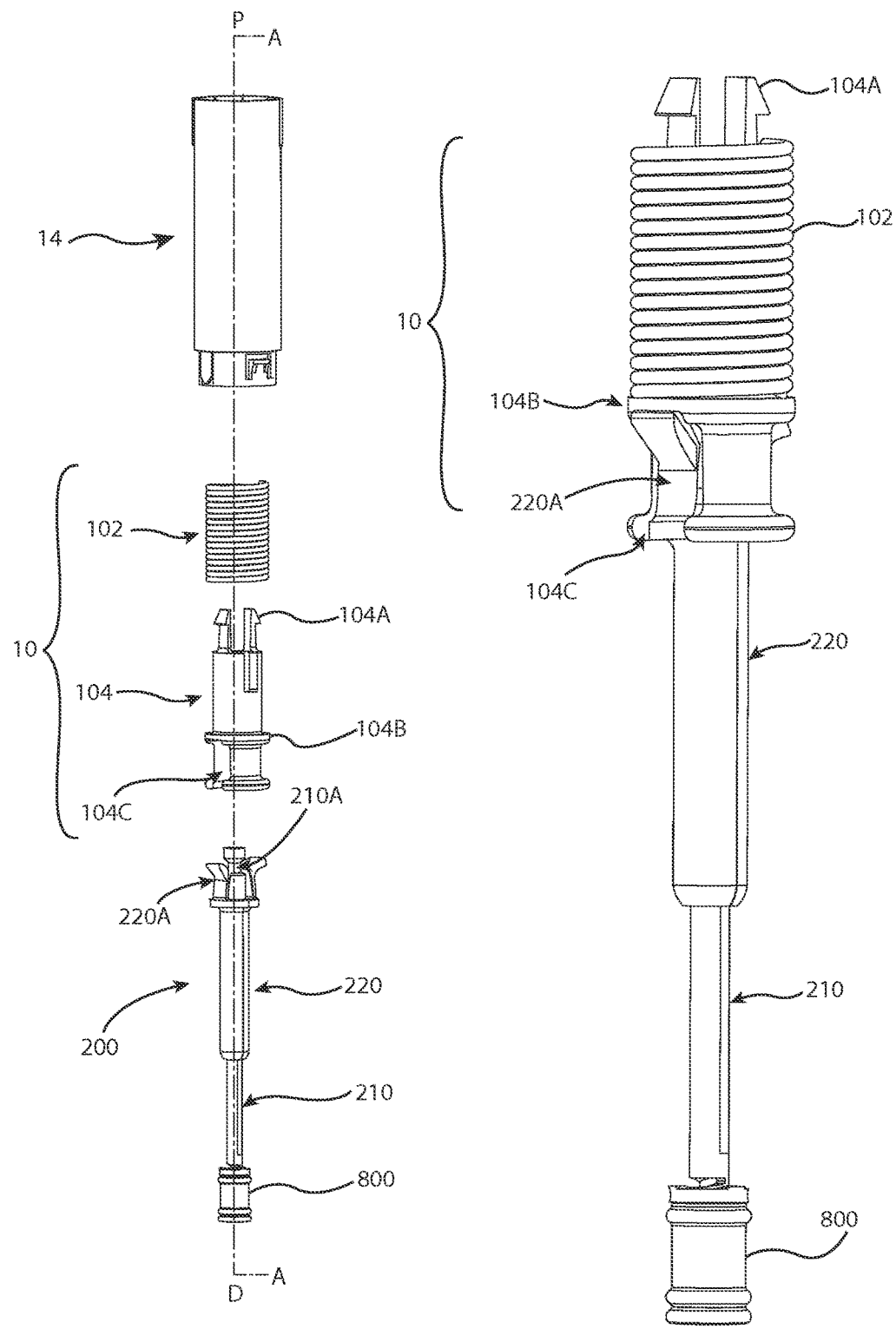
FIG. 3A shows an exploded view of an actuation mechanism and a plunger sub-assembly for an automatic injector, according to one embodiment of the present invention.
FIG. 3B shows an enlarged view of the actuation mechanism and the plunger sub-assembly shown in FIG. 3A in an energized state.
Figure 3C:
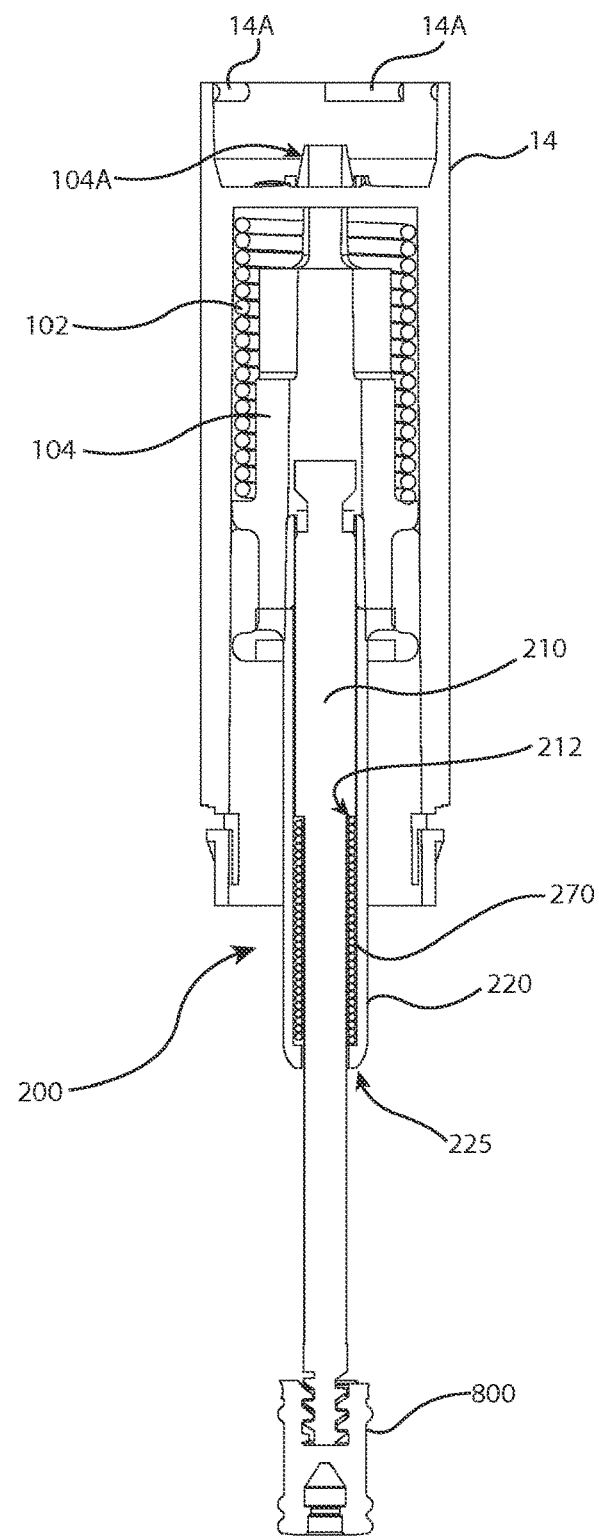
FIG. 3C shows a cross-sectional view of the actuation mechanism and the plunger sub-assembly shown in FIG. 3A.
Figure 3D:
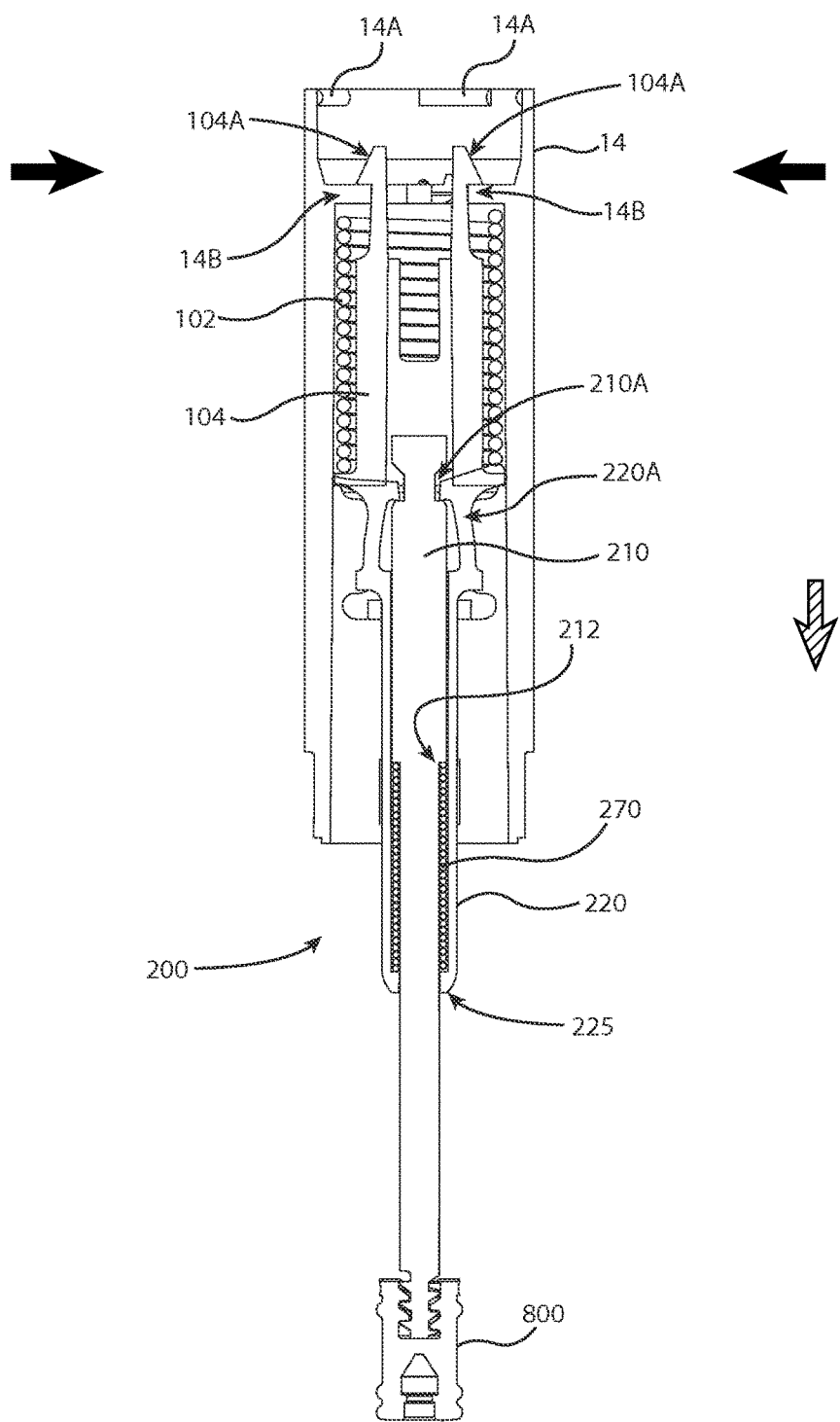
FIG. 3D shows a 90 degree rotation of the cross-sectional view shown in FIG. 3C.

FIGS. 3A-3D further detail the actuation mechanism 10 and the plunger sub-assembly 200, according to at least one embodiment of the present invention, which are components of the automatic injector. FIG. 3A shows the components of actuation mechanism 10 and plunger sub-assembly 200 in a partially exploded view, in addition to upper housing 14. FIG. 3B shows these components in an energized state prior to actuation. In at least one embodiment, actuation mechanism 10 includes actuation spring 102 and actuation pill 104. In an energized configuration prior to actuation, the actuation spring 102 rests in an energized state substantially around an upper portion of actuation pill 104. The actuation spring 102 is held in an energized state between, and upon activation caused to act on, a platform 104B of the actuation pill 104 and a lower portion of upper housing 14. In this energized configuration, actuation pill 104 is detachably connected to upper housing 14 within the interior of the lower portion of the upper housing 14, as shown in FIGS. 3C and 3D. The actuation pill 104 slidably or detachably engages plunger sub-assembly 200 to convey the force from, and distal translation of, the actuation pill to the plunger sub-assembly 200. In at least one embodiment, as shown in FIG. 3B, one or more engagement prongs 220A at the proximal end of a plunger outer 220 component of the plunger sub-assembly 200 contacts the actuation pill 104 within a distal slot 104C of the actuation pill 104. The actuation pill 104 has an interior axial pass-through within which a proximal portion of a plunger inner 210 component of the plunger sub-assembly 200 may initially reside and, upon activation of the retraction mechanism, may axially translate in the proximal direction without proximal movement of the plunger outer 220. As would be appreciated by one having ordinary skill in the art, the actuation spring and the actuation pill may be configured such that the actuation spring resides within an upper portion of the actuation pill. In such a configuration, the plunger inner component of the plunger sub-assembly may initially reside and, upon activation of the retraction mechanism, may axially translate in the proximal direction within the interior axial pass-through of the actuation pill and through an interior portion of the actuation spring. Regardless of the actuation spring and actuation pill configuration, the actuation pill slidably or detachably engages plunger sub-assembly to convey the force from, and distal translation of, the actuation pill to the plunger sub-assembly.

FIGS. 3C-3D provide cross-sectional views of the actuation mechanism 10 and plunger sub-assembly 200 at least partially within upper housing 14 prior to activation or actuation of the automatic injector. FIG. 3D shows a 90 degree axial rotation view of the view shown in FIG. 3C. As shown, locking hooks 104A of actuation pill 104 initially engage locking plateau 14B of upper housing 14. Upon activation of the automatic injector and actuation mechanism by the activation mechanism, locking hooks 104A are caused to disengage from locking plateau 14B. In at least one embodiment, the locking hooks 104A are moved radially inwards (i.e., in the direction of the solid arrows shown in FIG. 3D) by corresponding interface surfaces of the activation mechanism upon depression by the user, thereby causing disengagement of the actuation mechanism from the locking plateau 14B. As would be appreciated by an ordinarily skilled artisan, the term "hooks" is meant to reference any type of engagement mechanism including, for example, prongs, latches, tabs, and the like. Upon such disengagement, actuation spring 102 is permitted to expand from its energized state, thereby exerting force upon platform 104B of the actuation pill 104 and axially translating actuation pill 104 in the distal direction. Because actuation pill 104 is slidably or detachably engaged with plunger sub-assembly 200, such as by the interaction between one or more engagement prongs 220A at the proximal end of a plunger outer 220 component of the plunger sub-assembly 200 and the distal slot 1040 of the actuation pill 104, axial translation of the actuation pill 104 in the distal direction causes the plunger sub-assembly 200 to similarly axially translate in the distal direction (i.e., in the direction of the hatched arrow shown in FIG. 3D). Accordingly, the force asserted by the actuation spring 102 and the actuation pill 104 of the actuation mechanism 10, upon activation by the user, is utilized in the embodiments of the present invention to insert the needle into the user, to axially translate the plunger sub-assembly 200 in the distal direction to enable drug delivery, and to permit or facilitate activation of the retraction mechanism.

Figure 5:
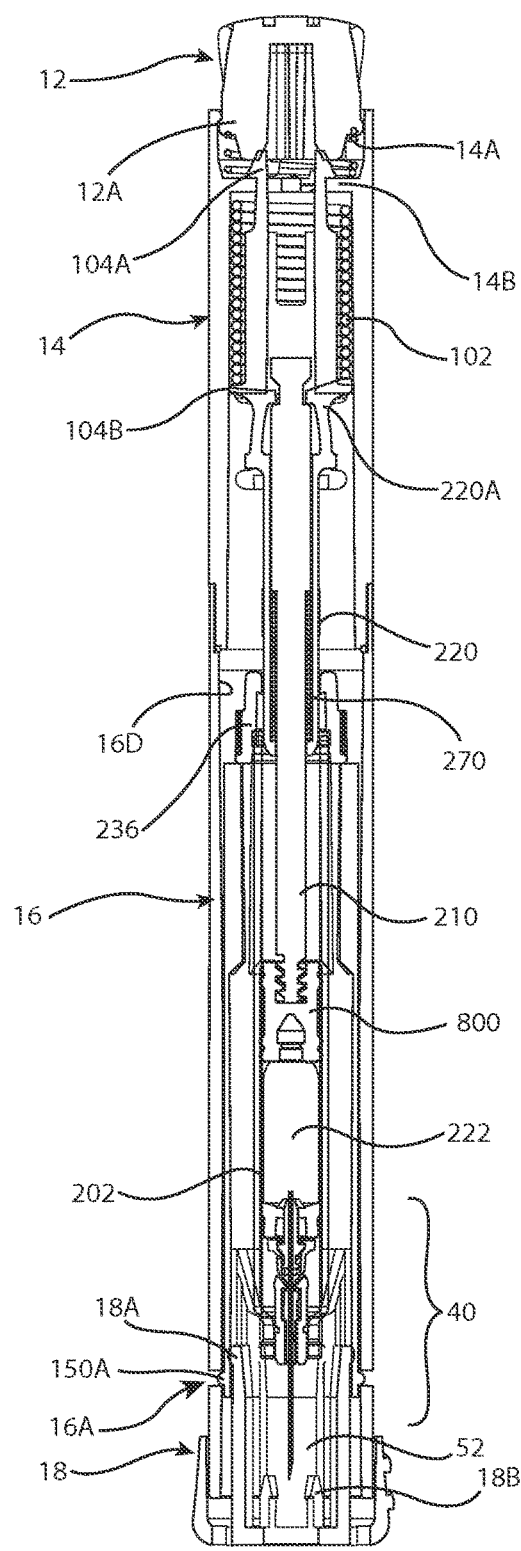
FIG. 5 shows an automatic injector including an actuation mechanism and a plunger sub-assembly, according to one embodiment of the present invention, in a locked configuration.
Figure 6A:
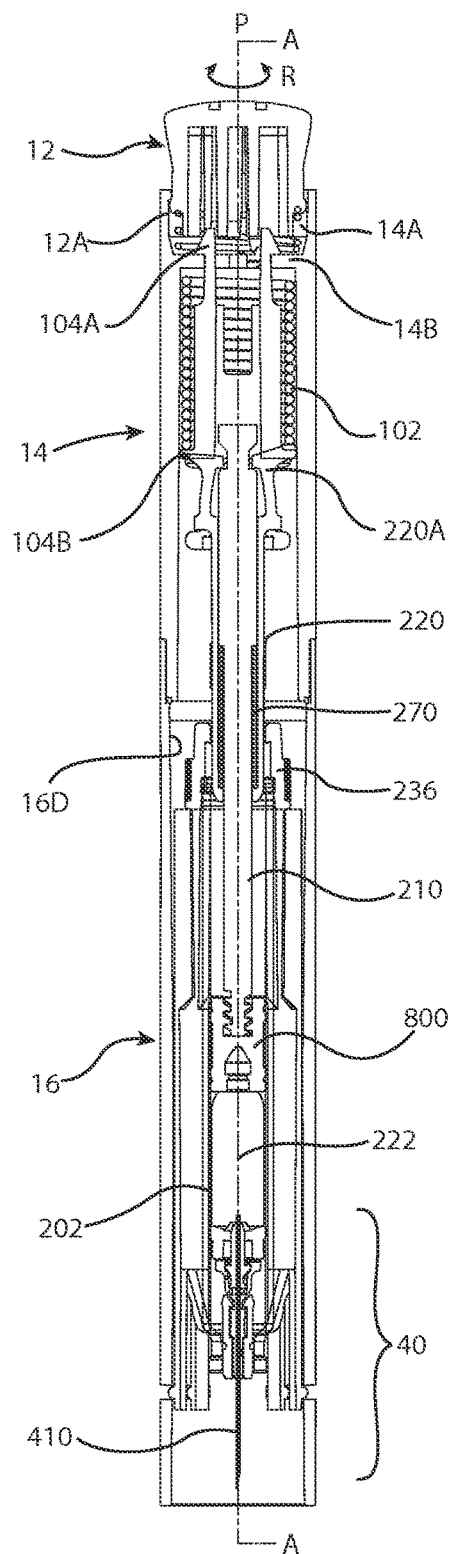
FIG. 6A shows an automatic injector including an actuation mechanism and a plunger sub-assembly, according to one embodiment of the present invention, in an unlocked configuration with the safety cap removed for needle insertion.
Figure 6B:
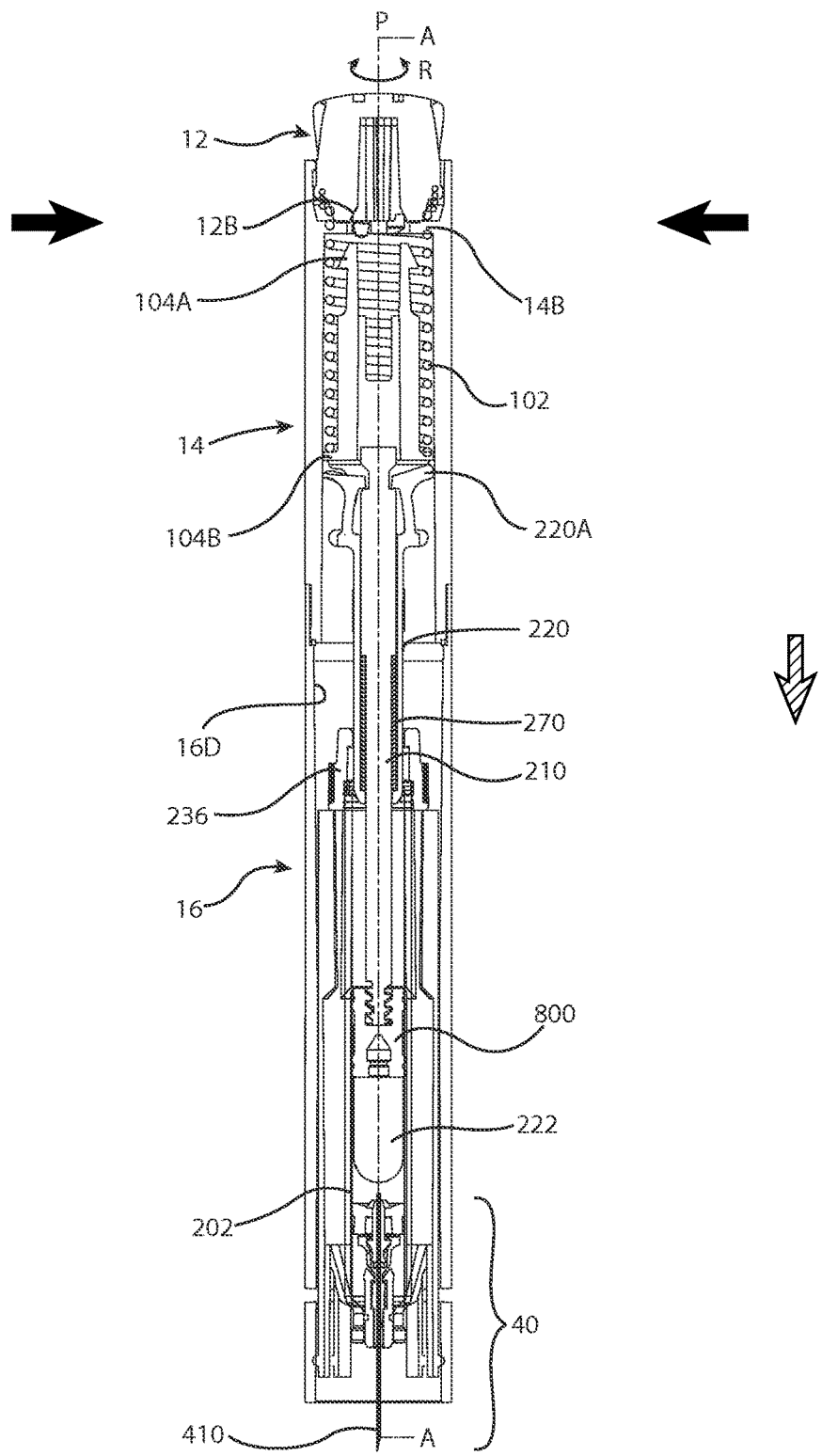
FIG. 6B shows an automatic injector including an actuation mechanism and a plunger sub-assembly, according to one embodiment of the present invention, in a needle insertion and drug dose delivery configuration.

Such operation of the actuation mechanism 10 is also shown in FIGS. 5, 6A, and 6B, in which actuation mechanism 10 is incorporated into an automatic injector 100. As shown in FIG. 5, release ring 236 rests upon the proximal end of sleeve 150 to retain the syringe barrel 202 and needle assembly 40 of the syringe cartridge in an initial locked position within the automatic injector 100. In at least one embodiment, sleeve 150 has one or more protrusion 150A that are initially held in position within corresponding notches 16A on the interior surface of lower housing 16. The notches 16A may be one or more separate notches, a notched ring around the interior circumference, or a number of other possible configurations which permit the one or more protrusions 150A to removably engage the notches 16A. In an initially locked configuration, locking extension 18A of the cap 18 rest against the interior surface of the sleeve 150 and assert a radially outward force to maintain the one or more protrusions 150A in engagement with notches 16A of the lower housing 16. Such an arrangement keeps the internal components of the automatic injector 100 in a substantially fixed and locked position capable of being stored and transported for extended periods of time. This configuration of the sleeve 150 also functions to maintain the position of the syringe barrel 202 and needle assembly 40 within the housing during, for example, removal of the needle shield 52. Additionally or alternatively, the sleeve 150 may be used to brace against barrel 202 of syringe cartridge 20 to ensure substantially axial alignment of these components during storage, transport, and operation of the actuation mechanism and automatic injector. Upon removal of the cap 18, protrusions 150A are permitted to flex radially inwards and disengage from the notches 16A. Accordingly, these components function as a safety feature and, upon removal of the cap 18, permit axial translation in the distal direction of the internal components of the automatic injector 100. The cap 18 may also include one or more surfaces 18B to engage needle shield 52 such that removal of the cap 18 by the user prior to activation also removes the needle shield 52 from the needle assembly.

Axial translation of the syringe cartridge may be associated with axial translation of the sleeve during other stages of operation, through the interaction between the release ring 236 of the syringe cartridge and the proximal end of sleeve 150. For example, upon removal of the cap 18 and activation of the automatic injector 100 by the user, the actuation mechanism 10 may cause syringe cartridge to move distally in the axial direction for needle insertion. Through the interaction between the release ring 236 and the sleeve 150, sleeve 150 is also caused to move distally in the axial direction. Sleeve 150 may be translated distally until a bridge portion 150B of sleeve 150 contacts a corresponding depth limiter 16B on the interior surface of the lower housing 16. Because of the interaction between release ring 236 and sleeve 150, limiting the range of motion of sleeve 150 also limits axial translation of release ring 236, syringe barrel 202, and syringe cartridge having a needle assembly 40. Accordingly, depth of needle insertion into a user can be controlled by the interaction between the bridge portion 150B of sleeve 150 and the depth limiter 16B of lower housing 16. For example, for intramuscular drug delivery (i.e., delivery into the muscle tissue of a user) the insertion depth may be greater and the depth limiter 16B may be located in a more distal position within the interior surface of the lower housing. For subcutaneous drug delivery, the depth limiter 16B may be located in a more proximal position within the interior surface of the lower housing and/or the bridge portion 150B of the sleeve 150 may be located at a more distal position of sleeve 150. FIG. 2 also shows these aspects of sleeve 150, lower housing 16, and cap 18 for additional clarity.

Figure 4:
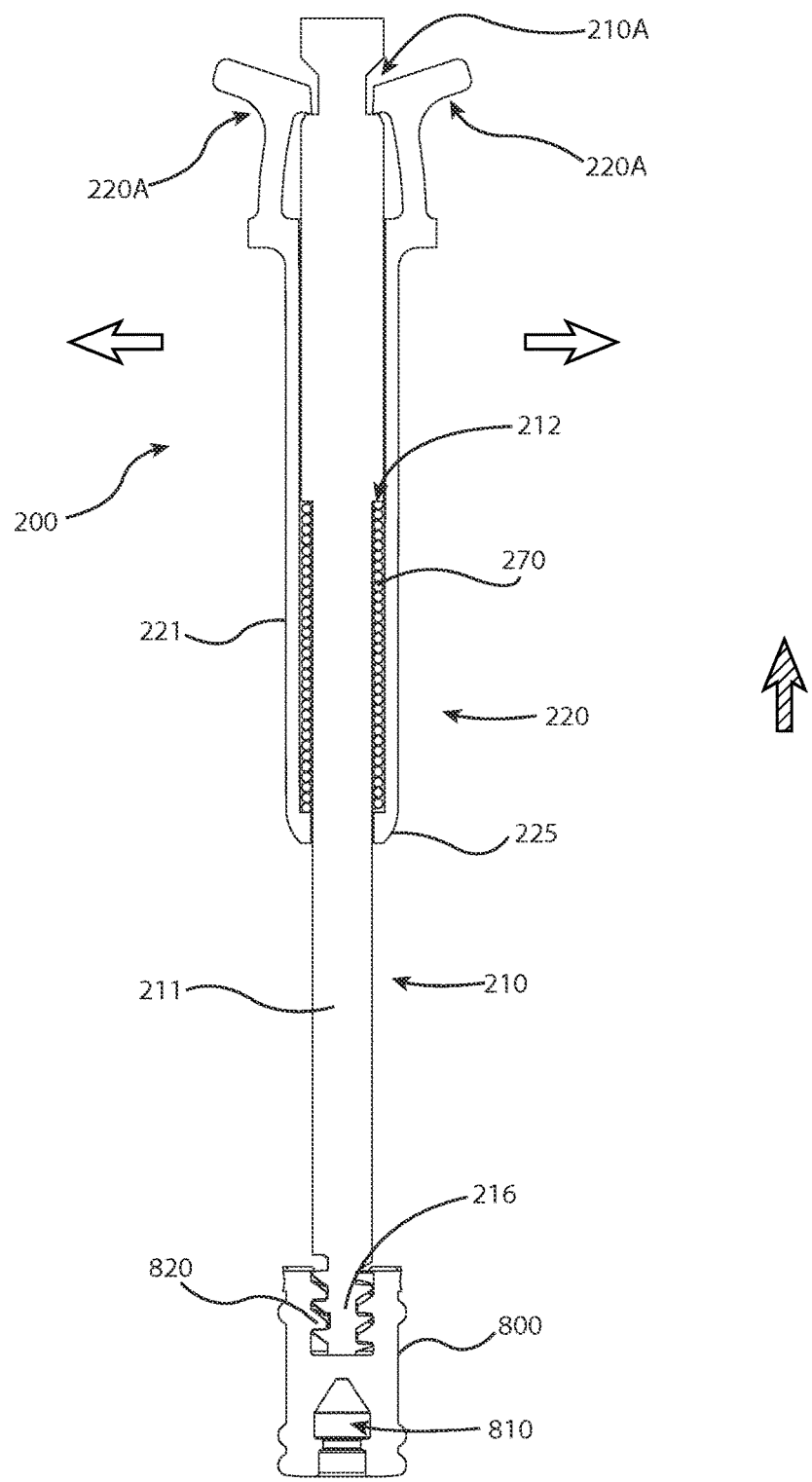
FIG. 4 shows a cross-sectional view of a plunger sub-assembly of an automatic injector, in a configuration capable of retracting a needle assembly upon or after completion of drug delivery, according to one embodiment of the present invention.

As described above, the embodiments of the present invention minimize the force necessary to initiate activation of the retraction mechanism. Because the plunger sub-assemblies and the integrated retraction features are driven, or caused to activate, by the actuation mechanism, the actuation mechanisms and the automatic injectors of the present invention may be configured to utilize lower force biasing members. This advantage of the novel plunger sub-assemblies of the present invention, and their integration into the actuation mechanism, provides substantial benefits to the manufacturability, stability, and operability of the novel automatic injectors described herein. In at least one embodiment, as shown in FIG. 4, the plunger sub-assembly 200 comprises plunger inner 210 comprising shaft 211, annular ledge 212, and seal-engaging member 216, which in this embodiment is a screw-threaded projection at the distal end of plunger sub-assembly 200. Seal-engaging member 216 engages complementary, screw-threaded recess 820 of plunger seal 800. Plunger seal 800 further comprises needle-engaging portion 810. Plunger sub-assembly 200 further comprises plunger outer 220 having elongate body 221 with base 225 and one or more engagement prongs 220A. Plunger sub-assembly 200 further comprises plunger spring 270 which is mounted between plunger inner 210 and plunger outer 220, and held in an initial first energized state between ledge 212 of plunger inner 210 and base 225 of plunger outer 220.

Initially, engagement prongs 220A are caused to releasably engage corresponding shoulder 210A at a proximal end of plunger inner 210. Engagement prongs 220A are held in releasable engagement with shoulder 210A by inward radial flexion caused by contact between the engagement prongs 220A and a first inner diameter or inner surface of upper housing 14. However, engagement prongs 220A of plunger outer 220 are resiliently flexible and flex radially outwards (in the direction of the hollow arrows shown in FIG. 4) when the engagement prongs 220A are no longer compressed or flexed radially inwards by the upper housing 14. This can occur, for example, when the plunger sub-assembly is caused to axially translate in the distal direction to a portion of the housing (e.g., the lower housing 16) having a second inner diameter or inner surface that is wider than the first inner diameter. Once the engagement prongs 220A disengage shoulder 210A of plunger inner 210, the plunger inner 210 is disengaged from plunger outer 220 to facilitate expansion of plunger spring 270 (in the direction of the hatched arrow shown in FIG. 4) from a first energized state to a second expanded state as part of the integrated retraction mechanism, as will be described hereinafter. Such novel embodiments of the plunger sub-assembly provide activation of the retraction mechanism without additional force being applied by the actuation mechanism. Accordingly, without additional force being applied by the actuation mechanism on the plunger sub-assembly, the retraction mechanism of the plunger sub-assembly is permitted to activate once the engagement prongs 220A reach a portion of the housing having a second inner diameter or inner surface that is wider than the first inner diameter. Preferably, the second inner diameter is located and dimensioned at a portion of the housing that suitably coincides with the plunger seal pushing out all of the drug fluid through the needle assembly and activation of the retraction mechanism. In at least one embodiment of the automatic injector, the second inner diameter is located in the upper housing, the lower housing, at the connection between the upper and lower housings, and/or at any portion of the housing that suitably coincides with the plunger seal pushing out all of the drug fluid through the needle assembly and activation of the retraction mechanism.

Figure 8:
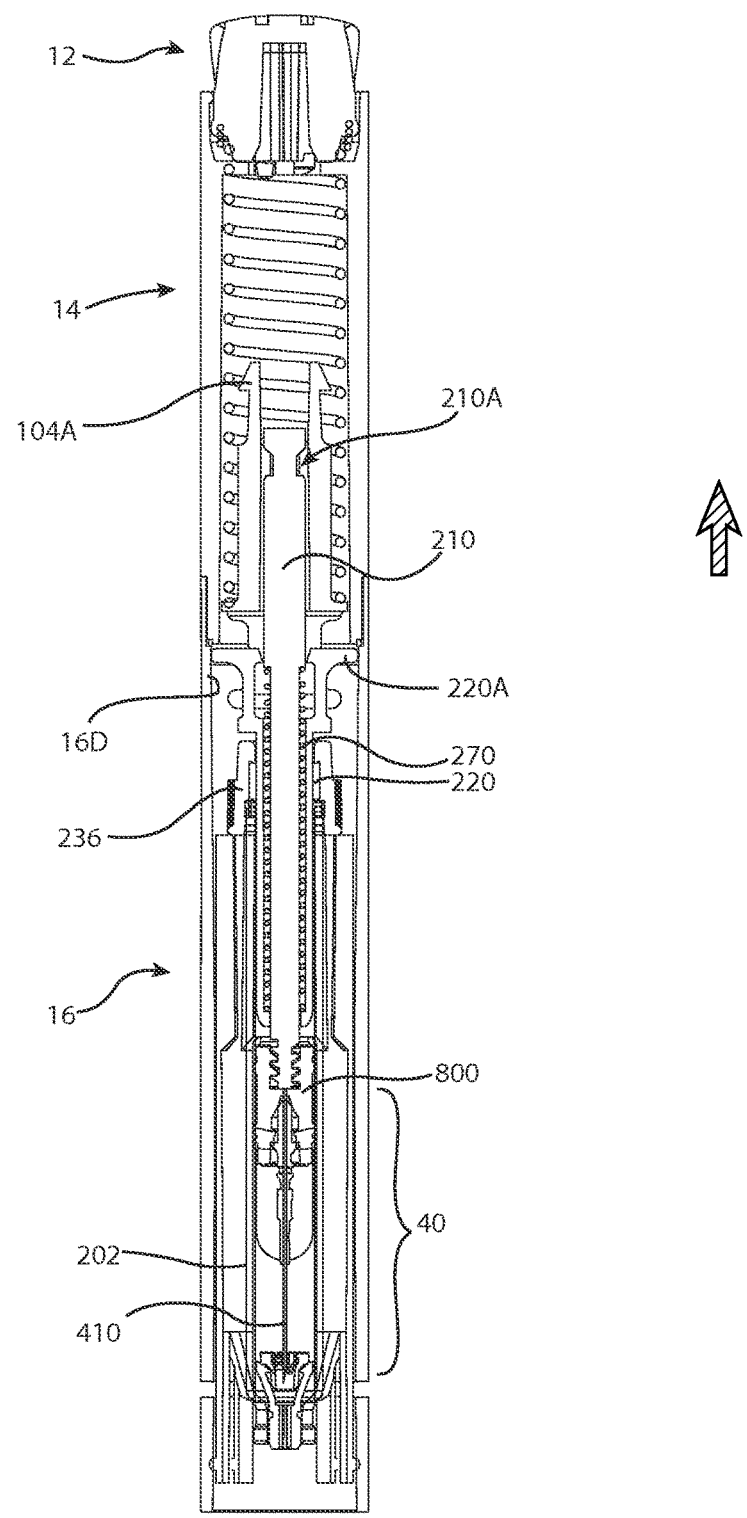
FIG. 8 shows an automatic injector including an actuation mechanism and a plunger sub-assembly, according to one embodiment of the present invention, in a second expanded state and retraction completed configuration.
Figure 9:
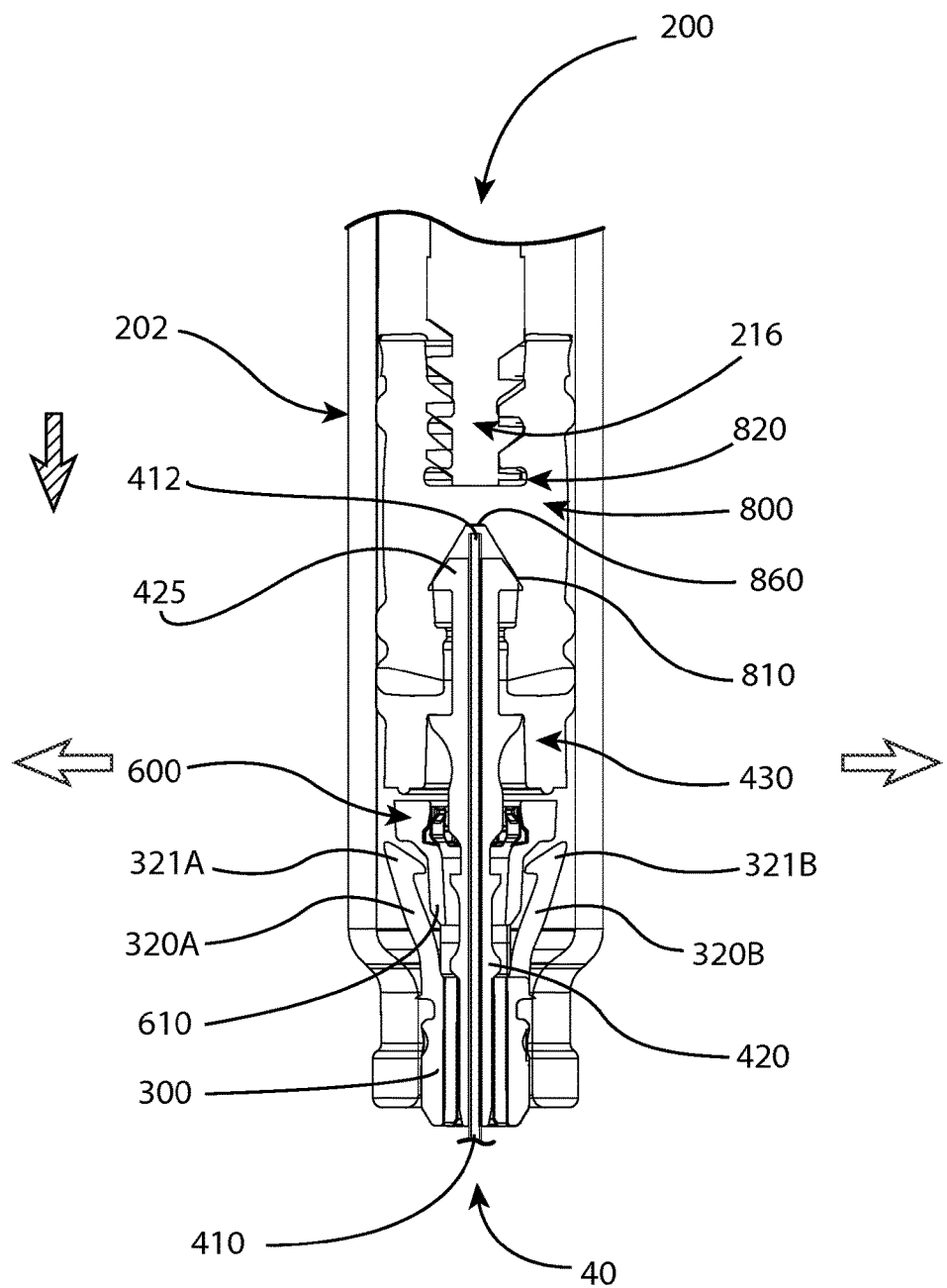
FIG. 9 shows an embodiment of a needle assembly engaged by a plunger prior to retraction.

In at least one embodiment needle assembly 40 integrates a retraction mechanism as described in International Publication WO2011/075760, which is incorporated by reference herein. As shown in FIG. 9, such a needle assembly 40 includes cannula 410, needle body 420, retainer 300, needle seal 430 and ejector 600. The needle assembly 40 is mounted into the distal end of barrel 202 of the syringe cartridge. FIG. 9 shows the components in the retraction activation stage, when contact between plunger seal 800 and needle seal 430, needle seal 430 and ejector 600, and ejector 600 and arms 320A, B of retainer 300 cause hook-ends 321A, B of retainer 300 to disengage from needle body 420 for retraction of needle assembly 40. Cannula 410 may be a number of fluid tubes but is preferably a rigid needle, such as a rigid steel needle. Prior to or upon retraction activation, plunger recess 860 of plunger seal 800 engages proximal segment 425 of needle body 420 for retraction of needle assembly 40. The retraction activation stage is detailed further with reference to the operation of automatic injector 100 in FIGS. 5-8 hereinafter. FIG. 9 shows just one embodiment of the needle assembly 40 configurable for use within an automatic injector 100. A number of other needle assemblies having integrated retraction mechanisms may similarly be utilized. For example, in at least one embodiment the needle assembly may integrate a retraction mechanism as described in U.S. patent application Ser. No. 13/693,915, which is incorporated herein by reference.

Operation of actuation mechanism 10, plunger sub-assembly 200, and automatic injector 100 will be described with particular reference to FIGS. 1-3 and 5-8. In these embodiments, drug chamber 222 of barrel 202 contains a fluid suitable for injection into a user. As evident in FIG. 5, safety cap 18 (shown also in FIG. 1A) is removable from lower housing 16 to allow activation of the device, insertion of the needle assembly, and drug delivery. Initially, activation mechanism 12 is in a locked configuration enabled by the releasable engagement between locking prongs 14A of upper housing 14 and locking grooves 12A of activation mechanism 12. Locking grooves 12A may be channels, recesses, detents, or the like along the radial circumference of the activation mechanism, as shown in FIG. 1B, within which locking prongs 14A may travel. Initially, the locking prongs 14A are in a position within the locking grooves 12A which prevents depression of the activation mechanism 12. The activation mechanism 12 may be rotated around the longitudinal axis to an unlocked position, where the locking prongs 14A are aligned with a portion of the locking grooves 12A that permits axial depression of the activation mechanism 12. Optionally, an activation spring 120 may be retained within the activation mechanism 12 and/or between the activation mechanism and the proximal end of the upper housing 14, for example to maintain the activation mechanism 12 in a locked position until user operation and to provide the user tactile resistance upon activation. This provides useful user feedback to ensure that the proper injection procedures are followed with the device and that removal of the cap is completed prior to needle insertion and drug injection.

In the configurations shown in FIG. 3D and FIG. 5, locking hooks 104A of actuation pill 104 initially engage locking plateau 14B of upper housing 14. After removal of the cap and unlocking of the activation mechanism, such as by axial rotation of the activation mechanism, the device may be placed in contact with the target location of the user and activated for needle insertion, drug delivery, and needle retraction. As described above, removal of the cap 18 may be configured to also remove needle shield 52 from the needle assembly. Similarly, removal of the cap 18 permits one or more protrusions 150A to flex radially inwards and disengage from the notches 16A of lower housing 16. Accordingly, removal of the cap 18 permits axial translation in the distal direction of the internal components of the automatic injector 100. Upon activation of the automatic injector and actuation mechanism by the activation mechanism, locking hooks 104A are caused to move radially inwards and disengage from locking plateau 14B. Upon such disengagement, actuation spring 102 is permitted to expand from its energized state, thereby axially translating actuation pill 104 in the distal direction. This stage initiates needle insertion into the patient and begins drug delivery to the patient.

FIGS. 6A and 6B show the automatic injector, in a cross-sectional view, before and after the device has been activated. Upon activation of the actuation mechanism, actuation spring 102 is permitted to expand from its energized state causing axial translation of the actuation pill 104 in the distal direction. Distal translation of actuation pill 104 causes distal translation of the plunger sub-assembly 200 through the interaction between engagement prongs 220A of the plunger sub-assembly 200 and the actuation pill 104 at distal slot 104C. At least initially, such distal translation causes the entire syringe cartridge to move with the sleeve 150 in the distal direction for needle insertion (i.e., in the direction of the hatched arrow in FIG. 6B), as shown in the transition between FIG. 6A and FIG. 6B. As described above, sleeve 150 may be translated distally until a bridge portion 150B of sleeve 150 contacts a corresponding depth limiter 16B on the interior surface of the lower housing 16. Because of the interaction between release ring 236 and sleeve 150, limiting the range of motion of sleeve 150 also limits axial translation of release ring 236, syringe barrel 202, and syringe cartridge having a needle assembly 40. Accordingly, depth of needle insertion into a user can be controlled by the interaction between the bridge portion 150B of sleeve 150 and the depth limiter 16B of lower housing 16.

Figure 7:
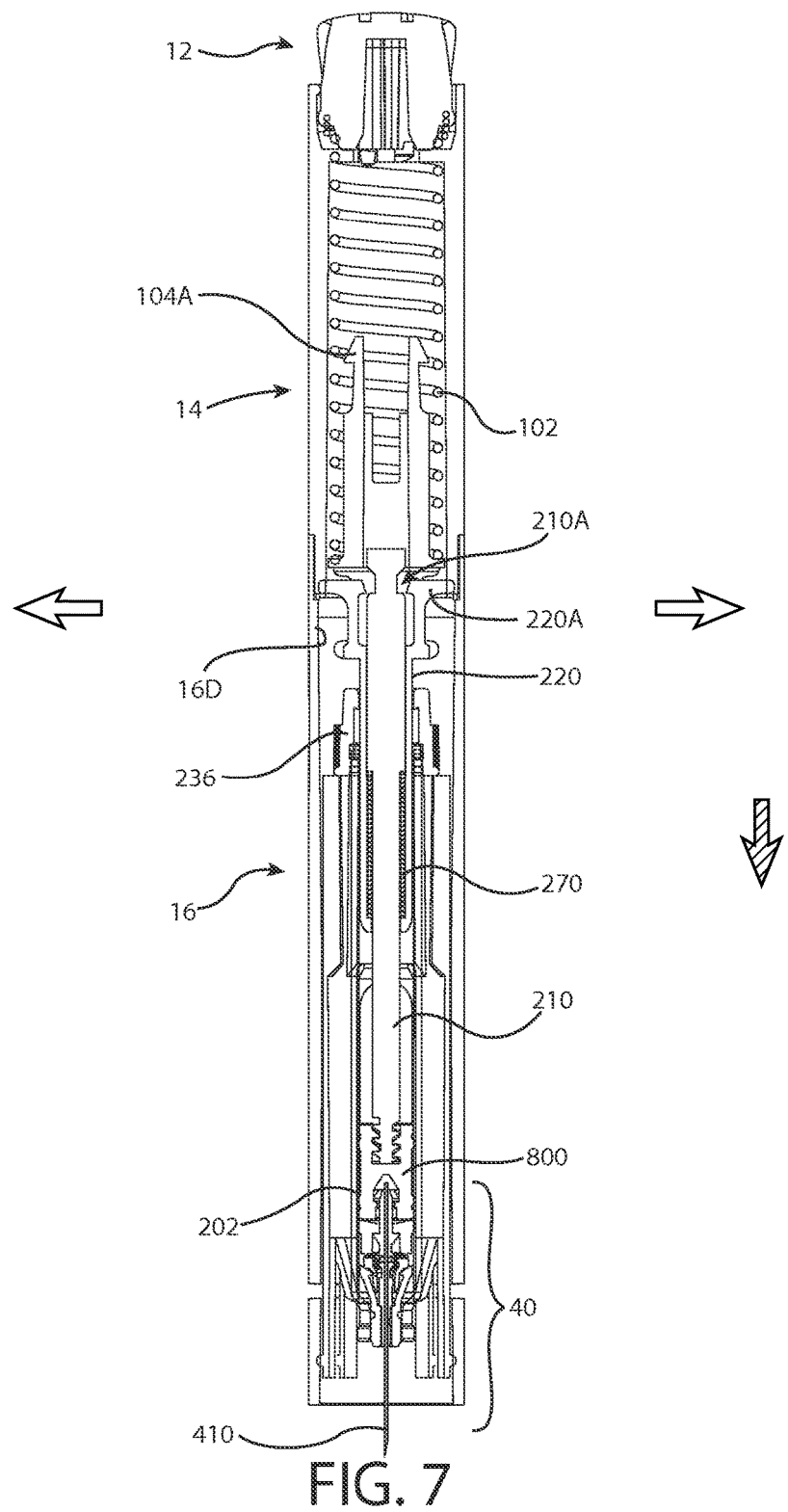
FIG. 7 shows an automatic injector including an actuation mechanism and a plunger sub-assembly, according to one embodiment of the present invention, in a retraction activated configuration.

As the sleeve 150 and syringe cartridge are prevented from further distal translation, the force applied by the actuation pill 104 on the plunger sub-assembly 200 causes plunger sub-assembly 200 to translate distally within the barrel 202 of the syringe cartridge. Because the syringe cartridge is prevented from further distal translation, distal translation of the plunger sub-assembly 200 within the barrel 202 causes a fluid, such as a liquid drug treatment, to be expelled from drug chamber 222 through cannula 410 of needle assembly 40 and into a user for drug delivery. This is visible in the transition between FIG. 6B and FIG. 7. The dimensions of the components and the lengths of axial travel within the device are configured such that engagement prongs 220A of the plunger sub-assembly 200 reach the second inner diameter, such as the interior recesses 16D of lower housing 16, substantially at the same time as or after activation of the retraction mechanism within the needle assembly 40. For example, as shown in FIG. 7, in at least one embodiment of the present invention the engagement prongs 220A reach the interior recesses 16D of lower housing 16 just after engagement between plunger seal 800 and needle seal of needle assembly 40, effectively ensuring that the recess of needle seal 800 has engagedly captured segment 425 of the needle body of the needle assembly 40 for retraction. The engagement prongs 220A are then able to flex radially outwards (i.e., in the direction of the hollow arrows in FIG. 7) and disengage from shoulder 210A of plunger inner 210 for activation of the retraction mechanism. As stated above however, the second inner diameter (e.g., interior recesses 16D) may be located in the upper housing, the lower housing, at the connection between the upper and lower housings, and/or at any portion of the housing that suitably coincides with the plunger seal pushing out all of the drug fluid through the needle assembly and activation of the retraction mechanism.

In at least one embodiment of the present invention, the needle retraction is essentially similar to that described in WO2011/075760, and will be briefly described as follows with reference to FIGS. 7-11. During delivery of fluid contents, plunger sub-assembly 200 moves axially through barrel 202 in the direction of the hatched arrow in FIG. 7. As shown in FIG. 9, plunger seal 800 bears against needle seal 430, which in turn bears against ejector 600. Further to this, ejector ring 610 moves hook-ends 321A, B of arms 320A, B of retainer 300 radially outwardly in the direction of the hollow arrows in FIG. 9, thereby disengaging needle body 420 from retainer 300 to release needle body 420 and cannula 410 for subsequent retraction. At this point, recessed seat 810 of plunger seal 800 has engaged segment 425 of retractable needle body 420 and recess 860 has received fluid end 412 of cannula 410. This effectively couples needle body 420 and cannula 410 to plunger inner 210 since plunger inner 210 is connected to the proximal end of plunger seal 800.

Figure 10:
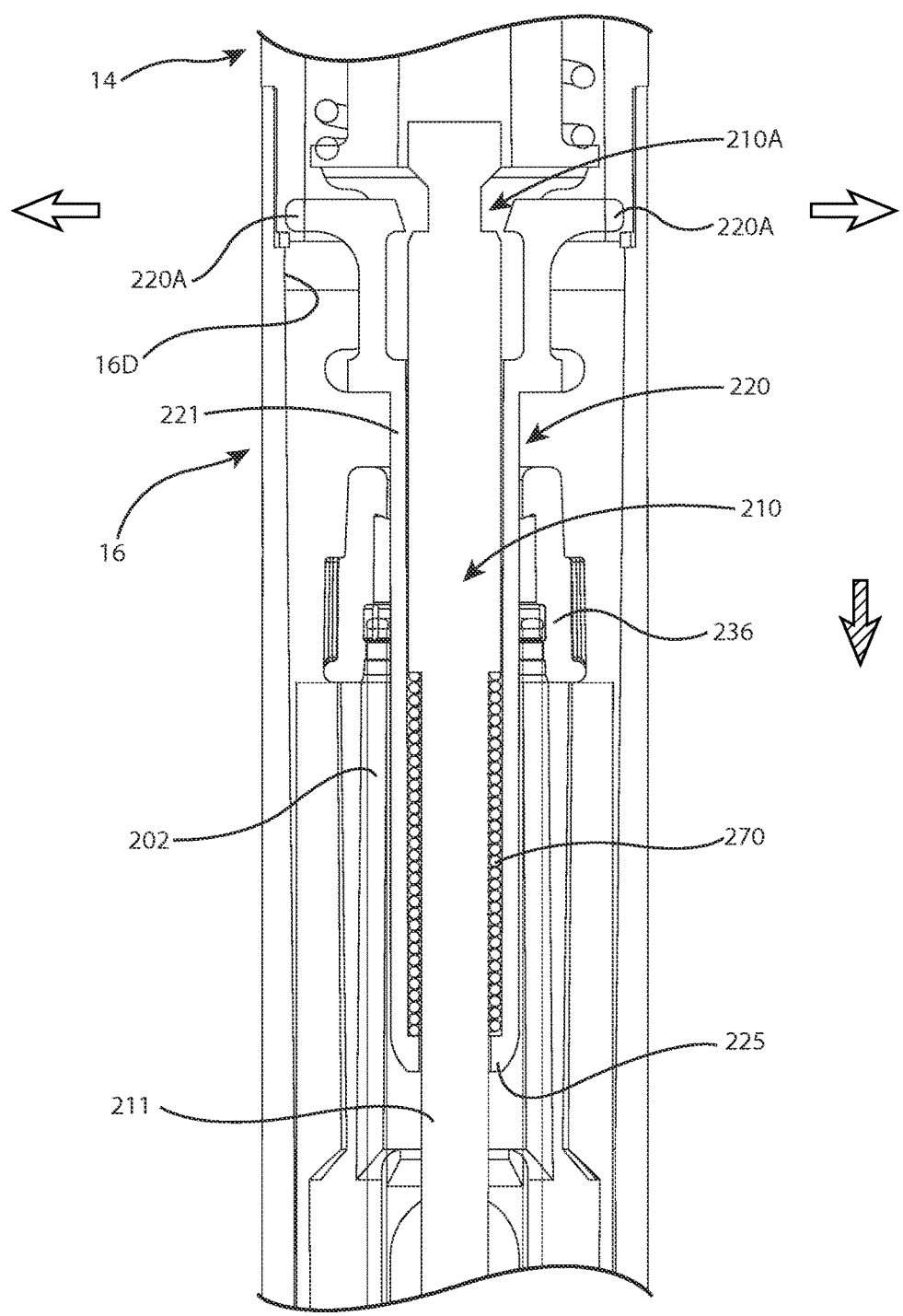
FIG. 10 shows an enlarged view of the retraction activated configuration shown in FIG. 7, in which a plunger outer disengages from a plunger inner to facilitate expansion of the retraction biasing member from its first energized state for needle retraction.
Figure 11:
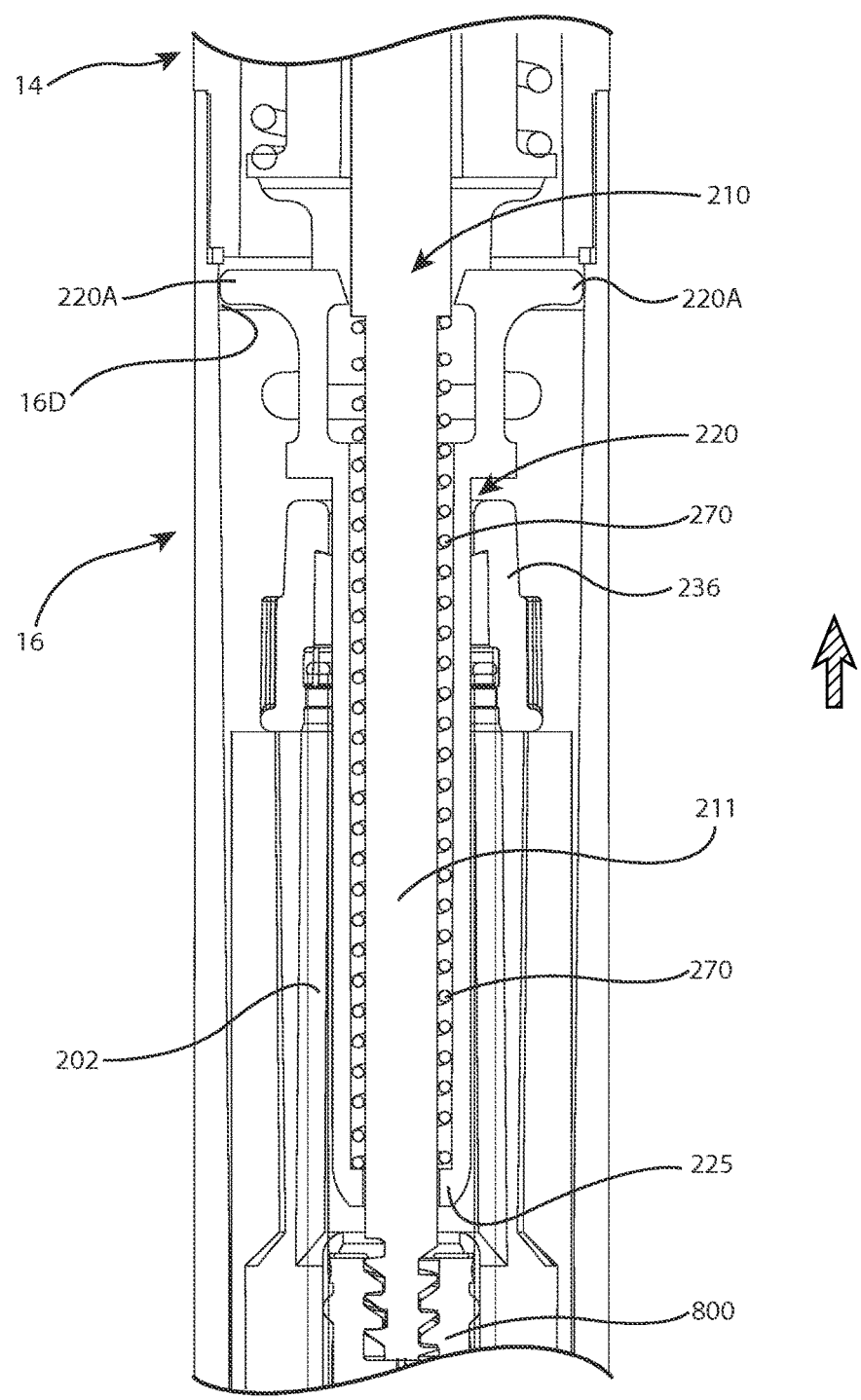
FIG. 11 shows an enlarged view of the second expanded state and retraction completed configuration shown in FIG. 8.

As shown in FIG. 7 and FIG. 10, in order for needle body 420 and cannula 410 to retract at the end of delivery of fluid contents, compressed spring 270 must decompress to a second expanded state, which is facilitated by plunger outer 220 disengaging from plunger inner 210. This disengagement is without additional force applied by the actuation mechanism 10 and, instead, simply by engagement prongs 220A of plunger outer 220 reaching a portion of the housing (e.g., the lower housing 16) having a second inner diameter or inner surface that is wider than the first inner diameter. Accordingly, without additional force being applied by the actuation mechanism on the plunger sub-assembly, the retraction mechanism of the plunger sub-assembly is permitted to activate once the engagement prongs 220A reach a portion of the housing having a second inner diameter or inner surface that is wider than the first inner diameter. FIG. 7 and FIG. 10 show this portion of the housing having a second inner diameter as recesses 16D of lower housing 16. As plunger inner 210 and plunger outer 220 are substantially fully depressed (i.e., axially translated in the distal direction as per the hatched arrow) to inject fluid from barrel 202, the engagement prongs 220A are permitted by the recesses 16D in lower housing 16 to flex radially outwards and disengage from shoulder 210A of plunger inner 210 (i.e., in the direction of the hollow arrows). This disengagement allows a plunger biasing member 270, such as a compression spring, to expand from its energized state and push against ledge 212 (shown in FIG. 4 and FIG. 10) of plunger inner 210 to thereby retract plunger inner 210 with plunger seal 800, needle body 420, and cannula 410 coupled thereto. Plunger outer 220 remains substantially in contact or connection with recesses 16D of lower housing 16, while plunger inner 210 coupled to needle body 420 and cannula 410 is axially translated in the proximal direction by decompression of spring 270, thereby retracting cannula 410 and needle body 420. The simplified design of the plunger sub-assembly 200 and the releasable engagement between engagement prongs 220A of plunger outer 220 and shoulder 210A of plunger inner 210 greatly reduces the force necessary for activation of the retraction mechanism. FIG. 8 and FIG. 11 show the components of the automatic injector with the plunger spring 270 in a second expanded state when needle retraction has completed. At this stage, cannula 410 is fully retracted into the housing and/or barrel 202 (i.e., in the direction of the hatched arrow in FIG. 8 and FIG. 11). This needle or cannula retraction is highly desirable as it provides integrated safety features while simultaneously providing a true end of dose indication to the user.

Certain optional standard components or variations of automatic injector 100 are contemplated while remaining within the breadth and scope of the present invention. For example, upper or lower housings may optionally contain one or more transparent or translucent windows 50, as shown in FIG. 1, to enable the user to view the operation of the automatic injector or verify that drug dose has completed. Additionally, an optional needle shield 52 may be utilized, as shown in FIG. 5, to protect cannula 410. The needle shield 52 may be connected, for example, to cap 18 and removed prior to operation of the automatic injector 100. Similarly, one or more of the components of automatic injector 100 may be modified while remaining functionally within the breadth and scope of the present invention. For example, as described above, while the housing of automatic injector 100 is shown as two separate components upper housing 14 and lower housing 16, these components may be a single unified component. Similarly, the interior surface of the housing may contain directional channels or guide paths within which the engagement prongs 220A may translate to ensure rotational alignment of the internal components during operation. Such standard components and functional variations would be appreciated by one having ordinary skill in the art and are, accordingly, within the breadth and scope of the present invention. It will be appreciated from the foregoing that the actuation mechanisms, plunger sub-assemblies, and automatic injectors disclosed herein provide an efficient and easily-operated system for automated drug delivery from a drug container, with integrated safety features and true end of dose indication to the user. Additionally the novel embodiments of the present invention minimize the force requirements for activation of the retraction mechanism, and thereby provide a simplified design for low force safety-integrated automatic injectors.

Assembly and/or manufacturing of actuation mechanism 10, plunger sub-assembly 200, automatic injector 100, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization fluids and processes may be employed during the manufacture of the novel components and devices. Furthermore, known sterilization processes may be employed at one or more of the manufacturing or assembly stages to ensure the sterility of the final product.

The automatic injector may be assembled in a number of methodologies. In one method, an actuation spring may be inserted into a housing and compressed between the housing and the actuation pill by detachably engaging one or more locking hooks of the actuation pill with a locking plateau of the housing. In this configuration, the actuation spring is initially maintained in an energized state substantially around an upper portion of the actuation pill. Alternatively, the actuation spring and the actuation pill may be configured such that the actuation spring resides within an upper portion of the actuation pill. Regardless of the actuation spring and actuation pill configuration, a syringe cartridge comprising a plunger sub-assembly, barrel, and needle assembly may be inserted into the housing such that a proximal end of the plunger sub-assembly contacts the actuation pill. Alternatively, the plunger sub-assembly may be connected to the actuation pill prior to insertion of the components into the housing. For example, the proximal end of the plunger outer may interface with a distal slot within the actuation pill. This enables, for example, rotational alignment of the plunger sub-assembly, prevents shifting of the plunger sub-assembly from a substantially axial alignment, and helps ensure an even distribution of force onto the plunger sub-assembly upon activation of the actuation mechanism. The syringe cartridge may be a number of syringes such as, for example, a prefilled syringe containing a drug treatment. Preferably, the syringe is a prefilled retractable syringe, as described above. The syringe barrel and needle assembly may be assembled into a lower portion of the housing separate from the upper portion containing the actuation mechanism and plunger sub-assembly. This assembly method may facilitate aseptic filling of the barrel within the housing, insertion of the plunger sub-assembly into the barrel, and connection of the upper and lower housing components for final assembly. The method may further include the step of: attaching an activation mechanism to the housing, wherein the activation mechanism is configured to contact the one or more locking hooks of the actuation pill upon activation. The activation mechanism may be positioned such that it is in a locked configuration for, for example, shipping and storage of the automatic injector. Additionally, the method may include the step of attaching a cap having a needle shield aspect, or attaching separate cap and needle shield, to the distal end of the syringe cartridge and automatic injector.

As discussed above, a glue or adhesive may be utilized to affix one or more components of the automatic injector to each other. Alternatively, one or more components of the automatic injector may be a unified component. For example, the upper housing and lower housing may be separate components affixed together by a glue or adhesive, a screw fit connection, an interference fit, and the like; or the upper housing and lower housing may be a single unified component. Similarly, in at least one embodiment of the present invention the actuation pill and the plunger outer may be a single unified component which detachably engages the plunger inner. Such a unified component would utilize one or more engagement prongs which are held in engagement with the plunger inner by the interior surface of the housing until the engagement prongs are axially translated to a portion of the housing having recesses or a second inner diameter which permits the engagement prongs to flex radially outwards to detach from the plunger inner. These components may be sterilized individually or together, and may be assembled in a sterile environment or sterilized after assembly. Similarly, the assembly of the embodiments of the present invention may utilize a number of other standard manufacturing practices.

The automatic injector may be utilized in a number of different ways. For example, in one embodiment the method of operating an automatic injector includes the step of: (i) disengaging one or more locking hooks of an actuation pill from a locking plateau of a housing, wherein such disengagement permits an actuation spring to expand substantially along a longitudinal axis of the housing from its initial energized state. The expansion of the actuation spring translates the actuation mechanism substantially along an axis of the automatic injector in the distal direction. Translation of the actuation mechanism causes translation of a plunger sub-assembly in the distal direction. As one or more engagement prongs of the plunger outer component of the plunger sub-assembly reaches one or more recesses in the inner surface of the housing, the engagement prongs are permitted to disengage from the corresponding shoulder of the plunger inner. In a preferred embodiment, this disengagement occurs when one or more engagement prongs of the plunger sub-assembly reach a portion of the housing having a wider interior diameter or recess, wherein this occurs just after engagement or contact between plunger seal 800 and needle seal of needle assembly 40. In at least one embodiment, this configuration effectively ensuring that the recess of needle seal 800 has engagedly captured segment 425 of the needle body of the needle assembly 40 for retraction. The actuation mechanism may initially drive the needle insertion and drug delivery into the patient. Subsequently, the actuation mechanism may activate the retraction mechanism of the syringe cartridge, as described above. The method may further include the steps of: operating the plunger sub-assembly of the automatic injector to deliver a substance to a recipient. Prior to step (i), the method may further include the step of: unlocking an activation mechanism and activating the activation mechanism, as described above.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

What is claimed is:

1. A low retraction activation force plunger sub-assembly for an automatic injector including a housing, a syringe cartridge, and an actuation mechanism configured to apply an injection force to the plunger sub-assembly to expel liquid from a drug chamber of the syringe cartridge, the plunger sub-assembly comprising: a plunger outer having at least one resiliently flexible engagement prong, a plunger inner having a shoulder, and a plunger biasing member retained in a first energized state between said plunger outer and plunger inner, wherein the at least one engagement prong of the plunger outer is configured to interface with a recess on an inner surface of the housing and flex radially outward to disengage from the shoulder of the plunger inner without an additional force applied by an actuation mechanism on the plunger subassembly, and wherein disengagement of the at least one engagement prong from the shoulder of the plunger inner allows the plunger biasing member to expand from the first energized state to a second expanded state to retract the plunger inner with respect to the plunger outer.

2. The plunger sub-assembly of claim 1, wherein the plunger biasing member is a compression spring.

3. The plunger sub-assembly of claim 1, wherein the plunger biasing member is held in the first energized state between a ledge of the plunger inner and a base of the plunger outer.

4. The plunger sub-assembly of claim 1, wherein the plunger inner has a seal-engaging member to engage a complementary engagement recess of a plunger seal.

5. The plunger sub-assembly of claim 1, wherein the plunger outer has two engagement prongs for releasable engagement with the shoulder of the plunger inner.

6. An automatic injector comprising a housing, an activation mechanism, an actuation mechanism, and a syringe cartridge having a plunger sub-assembly and a needle assembly, wherein the housing includes a recess on an inner surface of the housing, the actuation mechanism comprises an actuation biasing member residing in an initial energized state substantially within an upper portion of an actuation pill configured to apply an injection force to the plunger sub-assembly to expel liquid from a drug chamber of the syringe cartridge, and the plunger sub-assembly comprises a plunger outer having at least one resiliently flexible engagement prong, a plunger inner having a shoulder, and a plunger biasing member retained in a first energized state between said plunger outer and plunger inner, wherein the at least one engagement prong of the plunger outer is configured to interface with a recess on the inner surface of the housing and flex radially outward to disengage from the shoulder of the plunger inner without an additional force applied by the actuation mechanism on the plunger subassembly, and wherein disengagement of the at least one engagement prong from the shoulder of the plunger inner allows the plunger biasing member to expand from the first energized state to a second expanded state to retract the plunger inner with respect to the plunger outer.

7. The automatic injector of claim 6, wherein the actuation biasing member and the plunger biasing member are each a compression spring.

8. The automatic injector of claim 6, wherein the plunger biasing member is held in the first energized state between a ledge of the plunger inner and a base of the plunger outer.

9. The automatic injector of claim 6, wherein the plunger inner has a seal-engaging member to engage a complementary engagement recess of a plunger seal.

10. The automatic injector of claim 6, wherein the plunger outer has two engagement prongs for releasable engagement with the shoulder of the plunger inner.

11. The automatic injector of claim 6, wherein the actuation pill has at least one locking hook at a proximal end of the first actuation pill which initially engages a locking plateau at an interior proximal end of the housing.

12. The automatic injector of claim 11, wherein the activation mechanism is capable of engaging the at least one locking hook of the actuation pill to disengage the locking hook from the locking plateau of the housing.

13. The automatic injector of claim 6, wherein the syringe cartridge is a retractable syringe having a retractable needle assembly.

14. The automatic injector of claim 13, wherein the needle assembly comprises a cannula and needle seal.

15. The automatic injector of claim 14, wherein the plunger sub-assembly is capable of engaging the needle assembly to facilitate retraction of the cannula.

16. The automatic injector of claim 15, wherein retraction is facilitated by a plunger biasing member.

17. The automatic injector of claim 6, wherein the plunger sub-assembly, the actuation pill, and actuation biasing member are configured to permit the plunger inner to translate axially in the proximal direction through the actuation pill and the actuation biasing member upon disengagement of the engagement prong of the plunger outer from the shoulder of the plunger inner.

18. The automatic injector of claim 6, wherein the plunger sub-assembly is configured to enable contact between a plunger seal and a needle seal prior to, or substantially simultaneously upon, disengagement of the engagement prong of the plunger outer from the shoulder of the plunger inner to facilitate retraction of the needle assembly.

19. The automatic injector of claim 6 further comprising a sleeve having at least one protrusion that is initially held by a cap in an engaged position within corresponding notches on the interior surface of housing and, upon removal of the cap, protrusions are permitted to flex radially inwards to disengage from the notches.

20. The automatic injector of claim 19, wherein sleeve is configured to permit axial translation in a distal direction until a bridge portion of sleeve contacts a corresponding depth limiter on the interior surface of the housing.

21. The automatic injector of claim 6 further comprising at least one window within the housing, wherein the window is at least one of transparent, opaque, and translucent.

22. The automatic injector of claim 6 further comprising a tactile biasing member between the activation mechanism and the proximal end of the housing.

* * * * *